US00PP34316P2

(12) United States Plant Patent
Mowrey et al.

(10) Patent No.: US PP34,316 P2
(45) Date of Patent: Jun. 14, 2022

(54) BLUEBERRY PLANT NAMED 'DRISBLUETWENTYSEVEN'

(50) Latin Name: ***Vaccinium corymbosum* L.**
Varietal Denomination: DrisBlueTwentySeven

(71) Applicant: Driscoll's, Inc., Watsonville, CA (US)

(72) Inventors: Bruce D. Mowrey, Watsonville, CA (US); Esther J. Kibbe, Watsonville, CA (US); Marta C. Baptista, Watsonville, CA (US); Raymond L. Jacobs, III, Watsonville, CA (US); Maria Velarde, Watsonville, CA (US); James Olmstead, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/230,576

(22) Filed: Apr. 14, 2021

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

(56) References Cited

U.S. PATENT DOCUMENTS

PP6,699 P 3/1989 Wood
PP11,807 P2 3/2001 Lyrene
PP12,783 P2 7/2002 Lyrene
PP15,146 P3 9/2004 Hancock
PP19,503 P3 11/2008 Lyrene
PP20,436 P2 10/2009 Caster et al.
PP20,449 P2 11/2009 Caster et al.
PP20,488 P2 11/2009 Caster et al.
PP24,407 P3 4/2014 Caster et al.
PP24,489 P3 5/2014 Lyrene et al.
PP24,568 P3 6/2014 Caster et al.
PP24,569 P3 6/2014 Caster et al.
PP24,605 P3 7/2014 Caster et al.
PP26,287 P3 1/2016 Caster et al.
PP26,451 P3 3/2016 Rodriguez et al.
PP26,537 P3 3/2016 Caster et al.
PP26,643 P3 4/2016 Caster et al.
PP26,748 P3 5/2016 Rodriguez et al.
PP27,622 P3 1/2017 Caster et al.
PP28,933 P2 2/2018 Caster et al.
PP31,649 P2 4/2020 Caster et al.
PP31,650 P2 4/2020 Caster et al.
PP31,685 P2 4/2020 Mowrey et al.
PP31,698 P2 4/2020 Mowrey et al.
PP32,267 P2 10/2020 Caster et al.
PP32,744 P3 1/2021 Caster et al.
PP32,876 P2 3/2021 Mowrey et al.

*Primary Examiner* — Karen M Redden

(74) *Attorney, Agent, or Firm* — Morrison & Foerster LLP

(57) ABSTRACT

A new and distinct variety of blueberry plant named 'DrisBlueTwentySeven', particularly selected for the sweet flavor of its fruit, its adaptability for production in low latitudes, and appearance with persistent bloom, is disclosed.

5 Drawing Sheets

Latin name: Botanical classification: *Vaccinium corymbosum* L.

Varietal denomination: The varietal denomination of the claimed variety of blueberry plant is 'DrisBlueTwentySeven'.

BACKGROUND OF THE INVENTION

Blueberry plants are perennial flowering plants with indigo-colored berries from the section *Cyanococcus* within the genus *Vaccinium*. Many commercially sold species with English common names, including blueberry, are currently classified in section *Cyanococcus* of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L.), which has been denominated as 'DrisBlueTwentySeven'.

Blueberry plant variety 'DrisBlueTwentySeven' was discovered in Hillsborough County, Fla. in April of 2013 and originated from a cross between the proprietary female parent blueberry plant '53E3' (unpatented) and the proprietary male parent blueberry plant '147B2' (unpatented). The original seedling of the new variety was first asexually propagated via softwood cuttings and tissue culture in Santa Cruz County, Calif. in July of 2013.

'DrisBlueTwentySeven' was subsequently asexually propagated via softwood cuttings and tissue culture and underwent further testing in Santa Cruz County, Calif. for seven years (2014 to 2021). The present blueberry variety has been found to be stable and reproduce true to type through successive asexual propagations via softwood cuttings and tissue culture.

'DrisBlueTwentySeven' was selected for the sweet flavor of its fruit, its adaptability for production in low latitudes, and appearance with persistent bloom. 'DrisBlueTwentySeven' is a strongly evergreen variety with late season, high yield when grown under low latitude conditions. Fruit are large, moderately firm, and have excellent sweet flavor. Appearance is great after shipping due to persistent and heavy bloom. Plants are precocious and fruit predominantly on one-year-old shoots.

BRIEF DESCRIPTION OF THE DRAWINGS

This new blueberry plant variety is illustrated by the accompanying photographs. The colors shown are as true as can be reasonably obtained by conventional photographic procedures. The photographs are of plants that are six years old, unless otherwise specified.

DETAILED BOTANICAL DESCRIPTION

Figure 1:
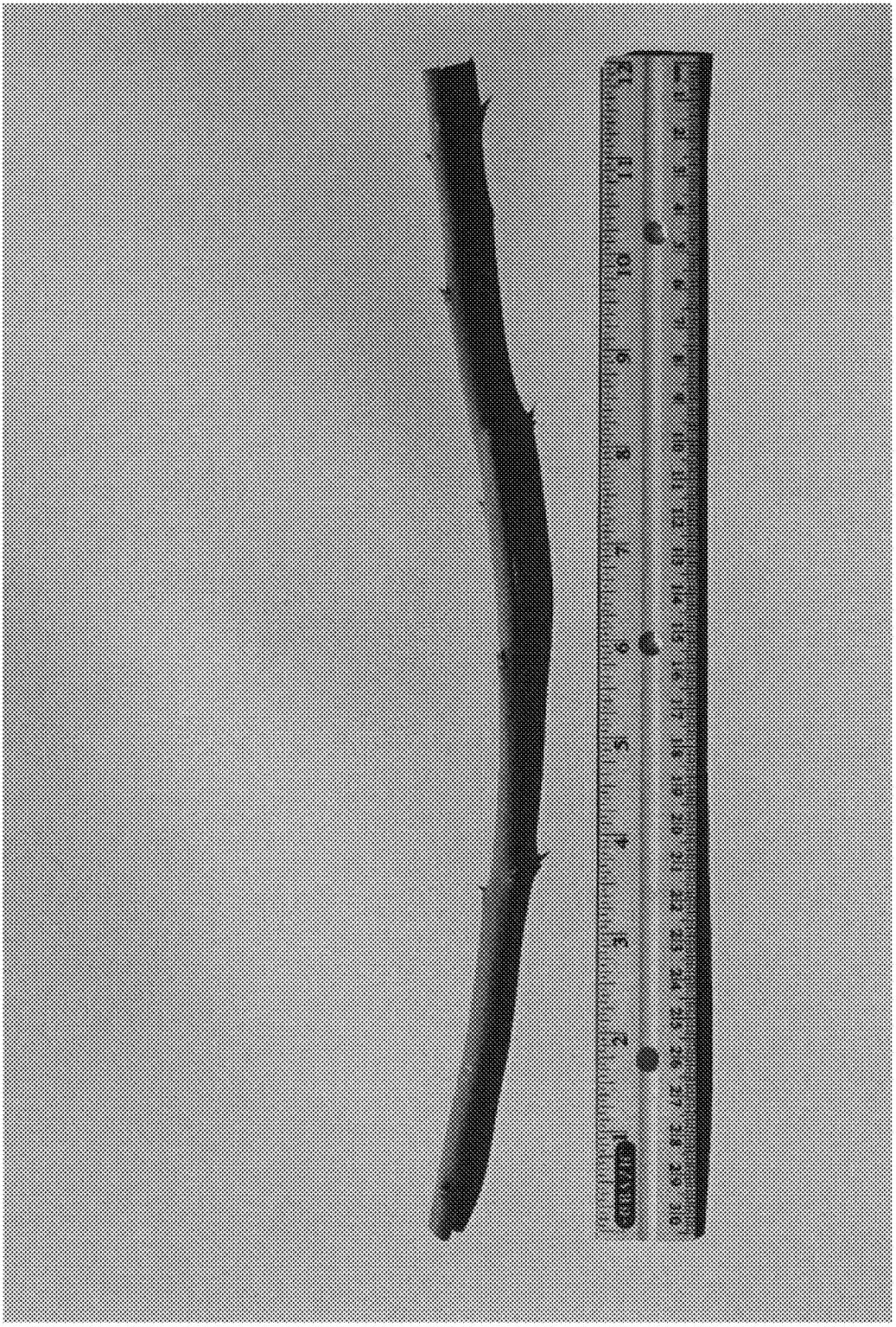
FIG. 1 illustrates a section of a cane of variety 'DrisBlueTwentySeven'.
Figure 2:
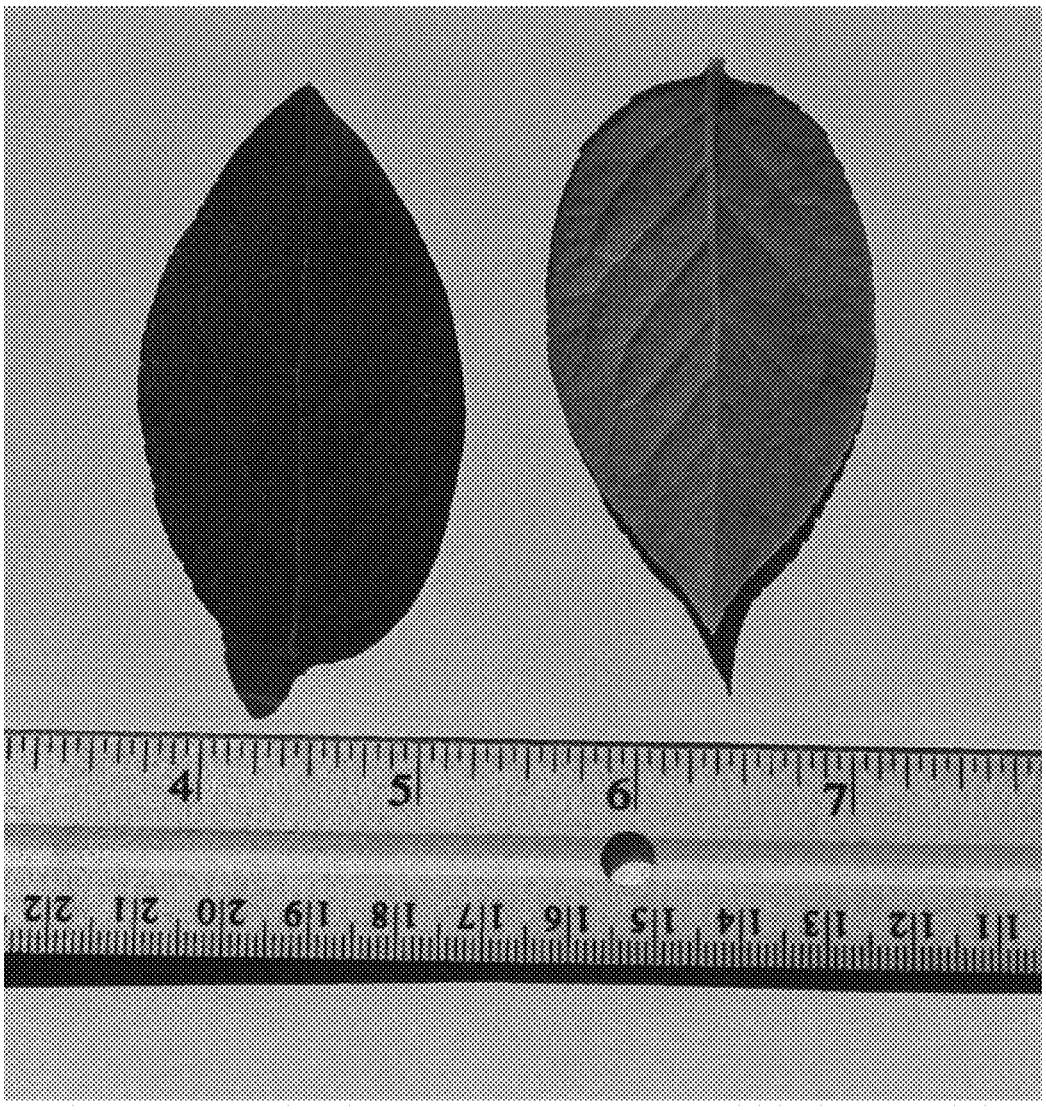
FIG. 2 illustrates leaves of variety 'DrisBlueTwentySeven'. The leaf on the left shows the upper leaf surface and the leaf on the right shows the lower leaf surface.
Figure 3:
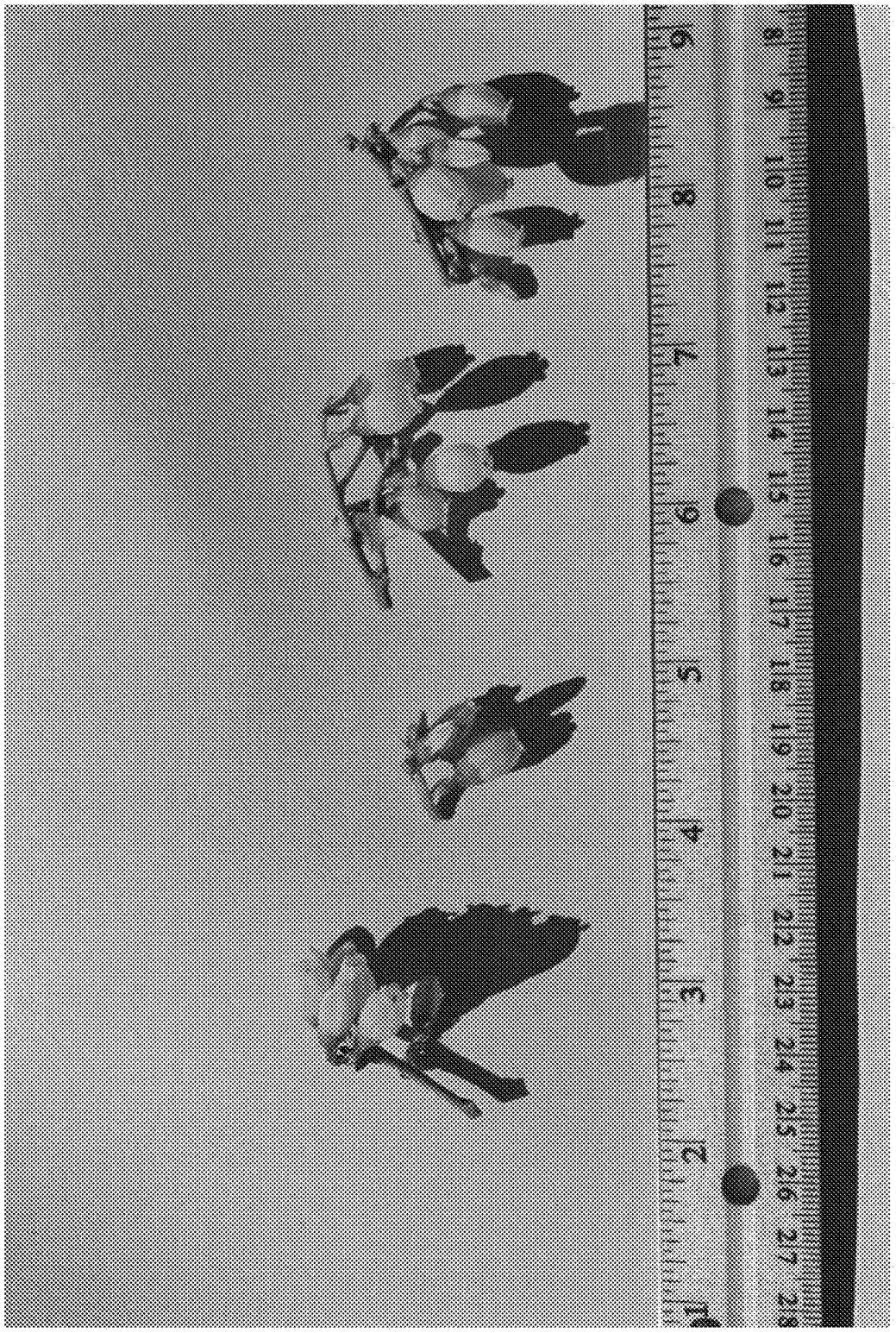
FIG. 3 illustrates clusters of flowers of variety 'DrisBlueTwentySeven'.
Figure 4:
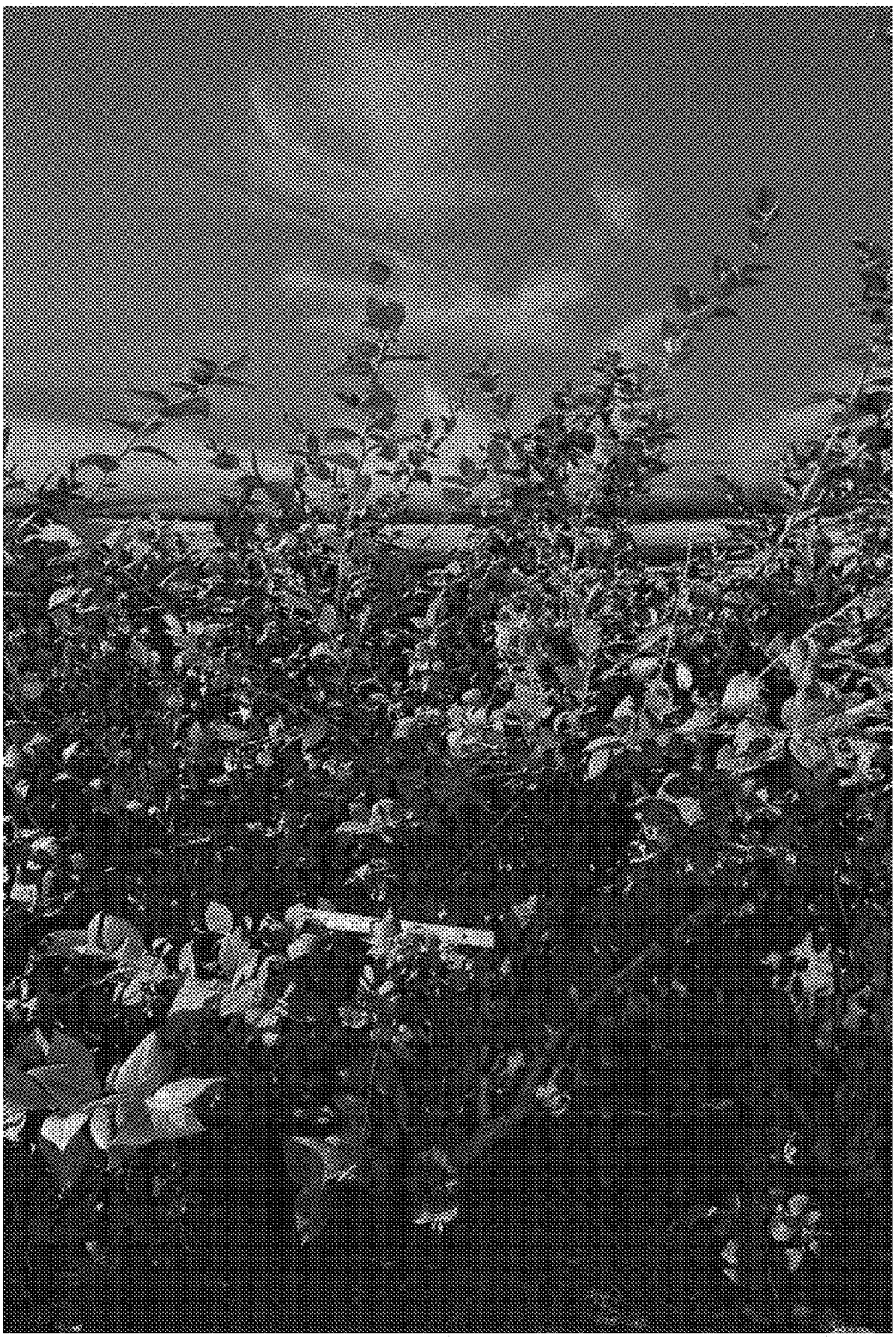
FIG. 4 illustrates whole plants of variety 'DrisBlueTwentySeven'.
Figure 5:
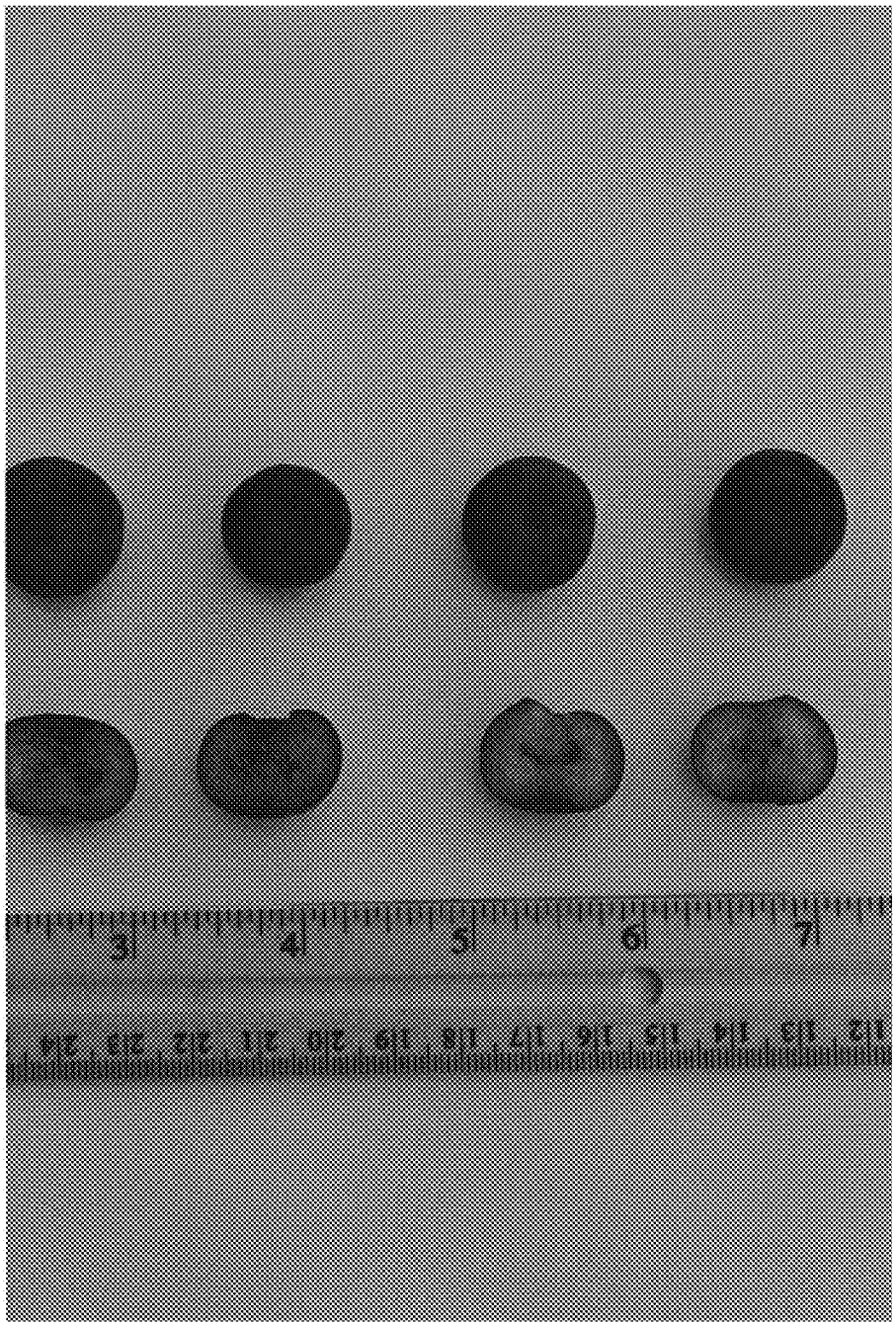
FIG. 5 illustrates whole and sliced fruit of variety 'DrisBlueTwentySeven'.

The following description sets forth the distinctive characteristics of 'DrisBlueTwentySeven'. The data which define these characteristics is based on observations taken in Santa Cruz County, Calif. from 2014 to 2021. This description is in accordance with UPOV terminology. Color designations, color descriptions, and other phenotypical descriptions may deviate from the stated values and descriptions depending upon variation in environmental, seasonal, climatic and cultural conditions. 'DrisBlueTwentySeven' has not been observed under all possible environmental conditions. Unless noted otherwise, the botanical description of 'DrisBlueTwentySeven' was taken from plants that were six years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family.*—Ericaceae.

*Botanical.*—*Vaccinium corymbosum* L.

*Common name.*—Blueberry.

*Variety name.*—'DrisBlueTwentySeven'.

Parentage:

*Female parent.*—Proprietary blueberry plant '53E3' (unpatented).

*Male parent.*—Proprietary blueberry plant '147B2' (unpatented).

Plant:

*Height.*—146.1 cm.

*Width.*—192.3 cm.

*Length/width ratio.*—0.76.

*Vigor.*—Strong.

*Growth habit.*—Semi-upright.

*Cane renewal.*—Weak.

*Chilling requirements.*—'DrisBlueTwentySeven' can be grown as a no-chill evergreen, but will require at least 300 hours of chilling below 7° C. for proper development if the plant goes dormant.

*Time of vegetative bud burst.*—Mid-March to May.

*One-year-old shoot* (*young canes*).—Length: 96.5 cm. Diameter at the base: 10.2 mm. Diameter at the tip: 2.9 mm. Internode length on the upper half: 35.2 mm. Color: RES 139C (Moderate yellow green). Texture: Smooth.

*Five-year-old shoot* (*mature canes*).—Length: 117.6 cm. Diameter at the base: 31.1 mm. Diameter at the tip: 8.2 mm. Internode length on the upper half: 48.4 mm. Color: RHS 199C (Light yellowish brown). Texture: Rough.

Leaves:

*Length.*—7.2 cm.

*Width.*—4.6 cm.

*Length/width ratio.*—1.6.

*Shape.*—Ovate.

*Margin.*—Entire.

*Apex shape.*—Cuspidate.

*Base shape.*—Obtuse.

*Arrangement.*—Alternate.

*Venation.*—Reticulate.

*Vein color.*—RHS 145B (Light yellow green).

*Color on upper side.*—RHS 139A (Dark yellowish green).

*Color on lower side.*—RHS 138C (Moderate yellow green).

*Glaucosity on upper side.*—Weak.

*Trichomes on upper side.*—Glabrous (absent).

*Glossiness.*—Dull.

*Petiole.*—Length: 3.2 mm. Diameter: 2.2 mm. Color: RHS 142C (Light yellow green).

*Sheath.*—Presence of leaf sheath: Present. Color: RHS 142C (Light yellow green).

Flowers:

*Flower length* (*excluding pedicel*).—11.7 mm.

*Flower width.*—6.1 mm.

*Flower length/width ratio.*—1.9.

*Color.*—RHS 155C (Greenish white).

*Fragrance.*—Medium.

*Inflorescence peduncle.*—Length: 44.2 mm. Diameter: 2.0 mm. Color: RHS 144D (Light yellow green).

*Flower bud.*—Length: 5.8 mm. Width: 2.8 mm. Number of flowers per bud: 4.2. Anthocyanin coloration: Medium. Anthocyanin color: RHS 59A (Dark red).

*Flower pedicel.*—Length: 5.4 mm. Diameter: 1.0 mm. Color: RHS 142D (Light yellow green).

*Corolla.*—Shape: Urceolate. Color of corolla tube: RHS 155C (Greenish white). Anthocyanin coloration of corolla tube on outer side: Weak. Anthocyanin color: RHS NN74B (Strong reddish purple). Conspicuousness of ridges on corolla tube: Weak. Color of receptacle: RHS 137A (Moderate olive green). Diameter of corolla aperture: 2.7 mm. Petal: Petal width (ridge to ridge): 2.7 mm. Color of the outer side: RHS 155C (Greenish white). Sepal: Length: 2.2 mm. Width: 2.7 mm. Color of the outer side: RHS 138C (Moderate yellow green).

*Reproductive organs.*—Style: Length (including stigma): 8.0 mm. Color: RHS 144B (Strong yellow green). Ovary: Color: RHS 138A (Moderate yellowish green). Stamen: Length: 6.4 mm. Color: RHS 144D (Light yellow green). Pollen: Amount: Medium. Pollen color: RHS 4D (Pale yellow green).

*Flowering interval on one-year-old shoot.*—Mid-March through May.

Fruit:

*Length.*—14.6 mm.

*Width.*—18.4 mm.

*Length/width ratio.*—0.79.

*Weight.*—2.8 grams/fruit.

*Shape in longitudinal section.*—Oblate.

*Attitude of sepals.*—Incurved.

*Calyx basin.*—Diameter: 6.3 mm. Depth: 3.2 mm. Diameter/depth ratio: 2.0.

*Infructescence* (*fruit cluster*).—Number of berries per cluster: 4.4. Density: Medium. Peduncle length: 59.8 mm. Peduncle diameter: 2.3 mm.

*Fruit pedicel.*—Length: 6.0 mm. Diameter: 1.5 mm.

*Color of unripe fruit.*—RHS 147D (Moderate yellow green).

*Intensity of bloom.*—Medium.

*Color of skin with bloom on mature fruit.*—RHS 100D (Very light purplish blue).

*Color of skin after removal of bloom on mature fruit.*—RHS 202A (Dark greyish purple).

*Flesh color.*—RHS 145C (Light yellow green).

*Fruit firmness.*—Medium.

*Fruit soluble solids* (*in °Brix*).—13.6.

*Seed.*—Diameter: 0.7 mm. Color: RHS 166B (Moderate reddish brown). Abundance: Medium.

*Fruiting.*—Fruiting type: On one-year-old shoots only. Harvest interval on one-year-old shoot: May to July. Yield: 1 kg to 2 kg of fruit per plant per season from 40-month old. plants when grown at Santa Cruz County, Calif. Market use of fruit: Fresh market.

Resistance to abiotic stress, pests, and diseases:

*Heat.*—Moderately resistant.

*Spotted-wing drosophila* (*Drosophila suzukii*).—Moderately susceptible.

*Botrytis fruit rot* (*Botrytis cinerea*).—Moderately susceptible.

COMPARISONS TO PARENTAL AND REFERENCE BLUEBERRY VARIETIES

'DrisBlueTwentySeven' differs from the female parent proprietary blueberry plant '53E3' (unpatented) in that 'DrisBlueTwentySeven' has earlier production and improved plant appearance compared to '53E3'. Further, fruit of 'DrisBlueTwentySeven' has a sweeter flavor than fruit of '53E3'. In addition, 'DrisBlueTwentySeven' has a lower chilling requirement than '53E3'.

'DrisBlueTwentySeven' differs from the male parent proprietary blueberry plant '147B2' (unpatented) in that 'DrisBlueTwentySeven' has improved plant appearance compared to '147B2'. In addition, fruit of 'DrisBlueTwentySeven' is larger and has a sweeter flavor than fruit of '147B2'.

'DrisBlueTwentySeven' differs from the reference blueberry plant variety 'DrisBlueSeven' (U.S. Plant Pat. No. 24,605) in that 'DrisBlueTwentySeven' has an ovate leaf shape, an obtuse shape of leaf base, a medium fragrance of flowers, and a medium intensity of bloom on mature fruit, whereas 'DrisBlueSeven' has an elliptic leaf shape, a cuneate shape of leaf base, a very faint or absent fragrance of flowers, and a very strong intensity of bloom on mature fruit.

'DrisBlueTwentySeven' differs from the reference blueberry plant variety 'DrisBlueThirteen' (U.S. Plant Pat. No. 26,451) in that 'DrisBlueTwentySeven' has weak cane renewal, an obtuse shape of leaf base, dull leaves, and a medium anthocyanin coloration on flower bud, whereas 'DrisBlueThirteen' has strong cane renewal, a cuneate shape of leaf base, glossy leaves, and a very strong anthocyanin coloration on flower bud.

What is claimed is:

1. A new and distinct variety of blueberry plant designated 'DrisBlueTwentySeven' as shown and described herein.

* * * * *